United States Patent [19]

Schubart et al.

[11] 3,959,284

[45] May 25, 1976

[54] BIS (2-BENTHIAZOLE-DITHIO)-N,N'-PIPERAZINES AND THEIR USE AS VULCANIZING AGENTS

[75] Inventors: Rüdiger Schubart; Ulrich Eholzer, both of Cologne, Germany

[73] Assignee: Bayer Aktiengesellschaft, Germany

[22] Filed: Mar. 28, 1972

[21] Appl. No.: 238,979

[30] Foreign Application Priority Data
Mar. 30, 1971  Germany............................ 2115294

[52] U.S. Cl........................ 260/268 BC; 260/306.5
[51] Int. Cl.²......................................... C07D 295/22
[58] Field of Search........ 260/268 S, 306.5, 268 BC

[56] References Cited
UNITED STATES PATENTS

| | | | |
|---|---|---|---|
| 2,837,519 | 6/1958 | Hardman | 260/268 S |
| 2,850,496 | 9/1958 | Hardman | 260/306.5 |
| 2,955,104 | 10/1960 | Smith | 260/268 S |
| 3,086,018 | 4/1963 | Hardman | 260/268 S |
| 3,133,920 | 5/1964 | Hardman | 260/306.5 |

OTHER PUBLICATIONS
Hofmann, "Vulcanization and Vulcanizing Agents," 1967, pp. 3, 286, The Garden City Press, TS 1891H6.
DuPont, "Blue Paper, Bl 191," 1945, TS 1925D9.

*Primary Examiner*—Raymond V. Rush
*Assistant Examiner*—David E. Wheeler
*Attorney, Agent, or Firm*—Connolly and Hutz

[57] ABSTRACT

The invention relates to bis (2-benzthiazole-dithio)-N,N'-piperazines of the general formula (I)

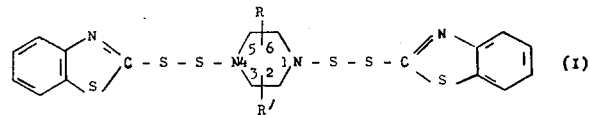

a process of their production and the use as a vulcanising agent for natural or synthetic rubber as well as a process for the vulcanisation of a natural or synthetic rubber.

3 Claims, No Drawings

BIS(2-BENTHIAZOLE-DITHIO)-M,M'-PIPERAZINES AND THEIR USE AS VULCANIZING AGENTS

The use of 4,4'-dithiomorpholine, optionally with accelerators (such as sulphenamides), for vulcanising natural and synthetic rubbers is known. In such cases the amount of sulphur employed is kept low (0 to 1.4 parts by weight to 100 parts by weight of rubber). 4,4'-dithiomorpholine is, however, not very stable in storage and decomposes within a few months at temperatures above room temperature.

The present invention is based on the discovery that bis-(2-benzthiazole-dithio)-N,N'-piperazines of the general formula (I):

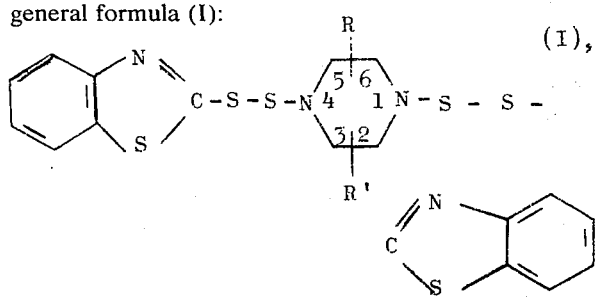

in which R and R' are the same or different and represent hydrogen or an alkyl group with 1 to 6 carbon atoms are suitable vulcanising agents or accelerators for natural and synthetic rubbers.

Compounds of the general formula (I) which are preferred are those in which the groups R are hydrogen or methyl and are in the 2,5- or 2,6- positions. Bis-(2-benzthiazole-dithio)-N,N'-piperazine, -2,5-dimethyl-piperazine, or -2,6-dimethyl-piperazine are particularly preferred compounds.

The object of this invention is thus a process for the vulcanisation of natural and synthetic rubbers in which a mixture of the rubber with 0.4 to 5 parts by weight of a bis-(2-benzthiazole-dithio)-N,'-piperazine of the general formula (I) to 100 parts by weight of the rubber is heated to temperatures of 100°C to 300°C.

A further object of the invention is a mixture containing a natural or synthetic rubber and 0.4 to 5.0 parts by weight of a bis-(2-benzthiazole-dithio)-N,N'-piperazine of the general formula (I), to 100 parts by weight of the rubber.

Particularly halogen-free rubbers containing C=C bonds are suitable for use in the process according to the invention. Natural rubber, diene rubbers, polyalkylene rubbers and ethylenepropylene terpolymers are more particularly suitable. Diene rubbers suitable for use according to the invention include, in particular, rubbers produced by the polymerisation or copolymerisation of halogen-free 1,3-dienes, preferably having 4–8 C atoms, for example, butadiene or isoprene. Examples of suitable comonomers are aromatic vinyl compounds, such as styrene, or acrylic acid or methacrylic acid derivatives, such as acrylonitrile or methacrylonitrile. Ethylene-propylene terpolymers are rubbers obtained by polymerization of ethylene, propylene and a non-conjugated diolefine. The non-conjugated diolefine, i.e. the ter component, can be present in amounts of up to 20 parts by weight in the polymer. Polyalkylenomer rubbers are rubbers obtained by ring-opening polymerization of cyclomonoolefines with the aid of mixed organometallic catalysts. Cis- and trans-polypentenamers, obtained by ring-opening polymerisation of cyclopentene, are especially suitable.

The bis-(2-benzthiazole-dithio)-N,N'-piperazines of formula (I) are new compounds. They can be prepared by reacting benzthiazole-2-sulphenamides with sulphur and a piperazine. Particularly suitable benzthiazole-2-sulphenamides are those of the general formula (II):

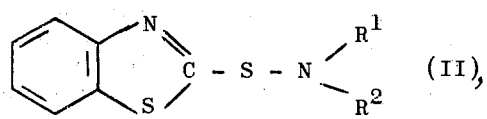

in which $R^1$ and $R^2$ are the same or different and each represent hydrogen, an alkyl group with 1–6 carbon atoms or a cycloalkyl group with 5 or 6 carbon atoms. Examples of such compounds are 2-amino-thio-benzthiazole, N-cyclohexyl-2-benzthiazole-sulphenamide, N-methyl-2-benzthiazolesulphenamide, N-ethyl-2-benzthiazole-sulphenamide, N,N'-dimethyl2-benzthiazole-sulphenamide, N,N'-diethyl-2-benzthiazole-sulphenamide, N-isopropyl-2-benzthiazole-sulphenamide, N,N'-dipropyl2-benzthiazole-sulphenamide, N-tert.-butyl-2-benzthiazole-sulphenamide and benzthiazole-2-sulphenmorpholide. Suitable piperazines are those having the general formula (III)

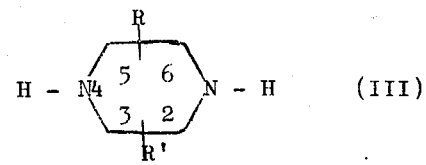

in which R and R' are the same or different and represent hydrogen or an alkyl group with 1–6 carbon atoms. Piperazine, 2,5-dimethylpiperazine and 2,6-dimethyl-piperazine are especially suitable. Mixtures of these compounds can also be used.

Examples of suitable solvents for the above reaction are alcohols, such as methanol, ethanol, n-propanol, isopropanol, n-butanol or isobutanol, hydrocarbons, such as benzene, toluene or xylene, dioxane, tetrahydrofuran and anisole.

The reaction can, for example, be carried out as it is shown in Example 5.

Bis-2-benzthiazole-dithio-N,N'-piperazines of formula (I) are highly effective vulcanising agents. They can therefore be employed alone. The vulcanisates are resistant to ageing and show a low residual deformation.

It is also possible, however, to use sulphur additionally in the vulcanisation, and in such cases preferably not more than 1.5 parts by weight sulphur, calculated on 100 parts by weight rubber, are employed.

The bis-(2-benzthiazole-dithio)-N,N'-piperazines are stable in storage even for several months at elevated temperatures. No decomposition or decrease of activity occurs. (cf. Example 3 below). The materials also retain their powdery consistency during storage and no stickiness, lumping or smell of amines is detected. A further indication of the high stability is the melting of, for example, bis-(2-benzthiazole-dithio)-N,N'-piperazine at 187°–188°C which is unusually high for a sulphenamide compound.

The compounds according to the invention are also relatively insensitive to acids and can thus be used in the presence of the acidic components sometimes present in vulcanising mixtures without any adverse effect on their activity.

A particular advantage of the bis-(2-benzthiazole-dithio)-N,N'-piperazines is that they not only act as vulcanising agents but at the same time also act as vulcanisation accelerators. It is, however, also possible to employ additional accelerators with the bis-(2-benzthiazole-dithio)-N,N'-piperazines. The usual accelerators from the thiazole group of compounds are particularly suitable for this purpose. Examples of these are N-cyclohexyl-2-benzthiazole-sulphenamide, N-tert.-butyl-2-benzthiazole-sulphenamide, 2-benzthiazole-thio-morpholine and 2-mercaptobenzthiazole. The zinc salt of 2-mercapto-benzthiazole and dibenzthiazoledisulphide can also be used. Additional accelerators from the thiuram group of compounds, e.g. tetramethyl-thiuram-disulphide, tetramethylthiuram-monosulphide or dimethyl-diphenyl thiuram-disulphide, can also be used with the compounds according to the invention. Thioureas such as diphenylthiourea, ethylenethiourea, diethylthiourea and dibutylthiourea are also suitable additional vulcanisation accelerators.

In general, bis-(2-benzthiazole-dithio)-N,N'-piperazines of the general formula (I) are used for the vulcanisation of rubbers in amounts of from 0.4 to 5.0 parts by weight per 100 parts by weight of the rubber.

The additional accelerators and vulcanising agents can be co-employed in the following amounts:

thiazole accelerators up to 2 parts by weight per 100 parts by weight rubber;

thioureas up to 1 part by weight per 100 parts by weight rubber;

sulphur up to 2.5 parts by weight per 100 parts by weight rubber and for particularly age-resistant vulcanisates up to 1.5 parts by weight per 100 parts by weight rubber.

The vulcanisation process is, in general, carried out in such a way that the bis-(2-benzthiazole-dithio)-N,N'-piperazines and optionally the other accelerators and vulcanisation agents are added to the rubber mixture separately or as a mixture. Vulcanisation is carried out, in general, at temperatures of 120° to 300°C preferably 140° to 240°C. Any of the usual vulcanisation plants may be employed for the process.

The rubbers may contain the usual additives such as fillers, such as carbon black, mineral oils, plasticisers, adhesives, accelerators, activators, such as stearic acid, wax, anti-ageing agents, anti-ozone agents, blowing-agents, dyes or pigments.

The vulcanisation process according to the invention is illustrated by the following examples. The test methods employed and the abbreviations used are given in Table 1. Table 2 gives the mixture tested.

Table 1

| Test methods | |
|---|---|
| 1) ti = scorch-time | by analogy with Mooney scorch-time (cf. DIN 53 524) obtained from the modulus-cure time curve. Increase of the modulus at 200 % elongation by 20 points above the minimum (step-cure) |
| 2) $M_{300}$-max. = modulus maximum | maximum modulus at 300 % elongation (kgf/cm$^2$), DIN 63 504, sheet 2 |
| 3) $t_{90}$ = total cure time | time (min.) taken to reach 90 % of the maximum modulus at 300 % elongation 150°C (step-cure) |
| 4) F = | tensile strength (kgf/cm$^2$), DIN 53 504, standard ring R 1 |
| 5) D = | elongation at break (%), DIN 53 540, sheet 1, standard R 1 |
| 6) H = | hardness (Shore a), DIN 53 505, range A, 4 mm pistons |
| 7) E = | rebound elasticity (%), DIN 53 512, 4 mm pistons |
| 8) Compression set (%) = | as in DIN 53 517; constant deformation 10 mm high cylinder 10 mm ⌀ Time: 22 hours/70°C and 70 hours/100°C. |

Abbreviations:
CBS = N-cyclohexyl-2-benzthiazole-sulphenamide
OBS = 4-(benzthiazole-2-sulphenyl)-morpholine
TBS = N-tert.-butyl-2-benzthiazole-sulphenamide
MBT = 2-mercaptobenzthiazole
ZMBT = zinc salt of 2-mercaptobenzthiazole
MBTS = dibenzthiazole-disulphide
TMTD = tetramethyl-thiuramdisulphide
TMTM = tetramethyl-thiurammonosulphide
MDS = 4,4'-dithiomorpholine Table 2

| Test mixture | parts per 100 parts of rubber (phr) |
|---|---|
| Natural rubber (smoked sheets) | 100.0 |
| Carbon black N 220 (ISAF) | 42.0 |
| Zinc oxide | 5.0 |
| Stearic acid | 3.0 |
| Aromatic mineral-oil plasticiser | 3.0 |
| Paraffin | 1.0 |
| Phenyl-β-naphthylamine | 1.0 |
| N-phenyl-N-isopropyl-p-phenylenediamine | 1.5 |

Example 1 shows the superiority of bis-(2-benzthiazole-dithio) -N,N'-piperazine according to the invention over 4,4'-dithiomorpholine (Nos. 1,3,5) corresponding values for which are quoted for comparison. At the same concentrations bis-(2-benzthiazoledithio)-N,N'-piperazine (Nos. 2,4,6) gives considerably higher maximum moduli, shorter total cure times ($t_{90}$) and better mechanical properties in the product. The compound according to the invention shows its superiority, however, particularly in resistance to reversion.

Example 2 shows the effectiveness of bis-(2-benzthiazoledithio)-N,N'-piperazine (mixture 8) as a vulcanisation accelerator. The compound according to the invention, at the same concentration, (0,4 phr), gives a considerably higher modulus, markedly better mechanical properties, especially tensile strength (F), and compression set, than the 4,4'-dithiomorpholine the corresponding values for which are given for comparison. Besides the higher modulus, the compound of the invention also has the advantage of a notably shorter cure time ($t_{90}$) than the 4,4'-dithiomorpholine (mixture 7) given for comparison.

Example 3 shows the superior stability in storage of bis-(2-benzthiazole-dithio)-N,N'-piperazine, which shows practically no diminution of activity after storage for 3 months at 50°C (mixtures 11 and 12), compared with 4,4'-dithiomorpholine, which shows a marked fall in activity after the same period of storage (mixtures 9 and 10).

Example 4 shows the effect of thioureas as supplementary accelerators on 4,4'-dithiomorpholine or bis-(2-benzthiazole-dithio)-piperazine. On comparing mixtures 13 and 14 it will be seen that bis-(2-benzthiazole-dithio)-piperazine (mixture 14) with supplementary diphenylthiourea gives better resistance to scorching, higher modulus and tensile strength and a considerably better reversion stability than 4,4'-dithiomorpholine (mixture 13). When ethylene thiourea (mixtures 15 and 16) is used, bis-(2-benzthiazoledithio)-piperazine (mixture 16) also gives better reversion stability and tensile strength than does 4,4'-dithiomorpholine (mixture 15).

EXAMPLE 1

(Natural rubber, test mixture see Table 2)

| Mixture No. | 1 | 2 | 3 | 4 | 5 | 6 |
|---|---|---|---|---|---|---|
| weight given in phr | | | | | | |
| 4,4'-dithiomorpholine | 3.8 | — | 1.5 | — | 0.5 | — |
| bis-(2-benzthiazole-dithio)-N,N'-piperazine | — | 3.8 | — | 1.5 | — | 0.5 |
| CBS | 0.5 | 0.5 | — | — | — | — |
| OBS | — | — | 0.6 | 0.6 | 0.5 | 0.5 |
| sulphur | — | — | 0.6 | 0.6 | 1.35 | 1.35 |
| scorch time at 130°C (min.) | 30 | 30 | 28 | 23 | 24 | 20 |
| maximum modulus ($M_{300}$) at 150°C (kgf/cm²) | 90 | 105 | 90 | 97 | 98 | 103 |
| total cure time $t^{90}$ at 150°C (min.) | 13 | 12 | 10 | 8.0 | 9.5 | 9.0 |
| resistance to reversion after 30 min./170°C (%) | 67 | 84 | 67 | 82 | 67 | 72 |
| F after $t_{90}$ + 10 min./150°C | 230 | 230 | 245 | 245 | 245 | 260 |
| D | 530 | 520 | 560 | 560 | 550 | 560 |
| H   units as in Table 1 | 59 | 65 | 58 | 61 | 60 | 61 |
| E | 51 | 53 | 50 | 52 | 50 | 52 |

EXAMPLE 2

Natural rubber with 42 parts carbon black N 220 (ISAF) per 100 parts of rubber, test composition given in Table 2 with additionally sulphur (2.35 phr, CBS: 0.5 phr)

| | No. 7 0.4 phr 4,4'-dithio-morpholine | No. 8 0.4 phr bis-(2-benzthiazole-dithio)-piperazine |
|---|---|---|
| scorch time at 120°C (min.) | 80 | 35 |
| scorch time at 130°C (min.) | 33 | 16 |
| maximum modulus ($M_{400}$) at 150°C (kgf/cm²) | 120 | 142 |
| total cure time $t_{90}$ at 150°C (min.) | 29 | 13 |
| resistance to reversion after 30 min/ 170°C (%) | 63 | 63 |
| F at $t_{90}$ + 10 min./150°C | 170 | 235 |
| D | 530 | 560 |
| H   units as in Table 1 | 52 | 60 |
| E | 42 | 46 |
| Compression set | | |
| 22 h/170°C heating stage 20min/150°C | 41 | 26 |
| 30 min/150°C | 37 | 22 |
| 70 h/100°C heating stage 20min/150°C | 92 | 68 |
| 30 min/150°C | 88 | 56 |

EXAMPLE 3

Storage test: 3 months at 50°C
Test composition as in Table 2 with additionally CBS 0.5 phr

| Vulcanising agent | Amount (phr) | $M_{300}$-max at 150°C | F | D | H | E | |
|---|---|---|---|---|---|---|---|
| | | | at 150°C/30 min. units as in Table 1 | | | | |
| No. 9 4,4'-dithio-morpholine | 3.8 | 100 | 240 | 530 | 62 | 50 | fresh material, Mp: 122°C |
| No. 10 4,4'-dithio-morpholine[1] | 3.8 | 72 | 180 | 630 | 56 | 42 | after 3-months storage at 50°C |
| | | 72 % residual modulus maximum in % of the initial value | | | | | |
| No. 11 bis-(2-benz-thiazole-dithio)-N,N'-piper-azine | 3.8 | 118 | 255 | 535 | 63 | 52 | fresh material Mp: 187 – 188°C |

-continued

| Vulcanising agent | Amount (phr) | $M_{300}$-max at 150°C | F | D | H | E |
|---|---|---|---|---|---|---|
| | | | at 150°C/30 min. units as in Table 1 | | | |
| No. 12 bis-(2-benz-thiazole-dithio)-N,N'-piper-azine[2] | 3.8 | 117 | 250 | 530 | 63 | 52 after 3-months storage at 50°C |
| | | 99 % residual modulus maximum in % of the initial value | | | | |

[1]material after 3-months storage sticking together, glutinous, smelling of amine. M.p. 110 – 118°C (sintered above 95°C)

[2]material after 3-months storage powdery, dry, odourless, M.p. 187 – 188°C

EXAMPLE 4

Natural rubber: mixture as given in Table 2 with additionally 0.6 parts OBS per 100 parts rubber

| Vulcanising agent | (phr) | thiourea (phr) | sulphur (phr) | scorch time at 120°C (min). | maximum modulus ($M_{300}$) at 150° (kgf/cm²) | total cure time $t_{90}$ at 150 (min.) | resistance to reversion after 30 min./170°C (%) | F | D | H | E |
|---|---|---|---|---|---|---|---|---|---|---|---|
| | | | | | | | | at $t_{90}$/150°C units as in Table 1 | | | |
| No. 13 4,4'-di-thiomor-pholine | 1.5 | diphen-ylthio-urea 0.5 | 0.6 | 16 | 94 | 9 | 71 | 255 | 570 | 56 | 51 |
| No. 14 bis-(2-benzthia-zole-di-thio)-pi-perazine | 1.5 | diphen-ylthio-urea 0.5 | 0.6 | 22 | 100 | 8 | 81 | 270 | 590 | 59 | 52 |
| No. 15 4,4'-di-thiomor-pholine | 1.5 | ethylene thiourea 0.5 | 0.6 | 24 | 101 | 9.5 | 72 | 245 | 570 | 57 | 51 |
| No. 16 bis-(2-benzthia-zole-di-thio)-pi-perazine | 1.5 | ethylene thiourea 0.5 | 0.6 | 23 | 102 | 8.5 | 83 | 270 | 590 | 60 | 51 |

EXAMPLE 5

Bis-(2-benzthiazole-dithio)-N,N'-piperazine 45.5 g (0.25 mol) 2-aminothiobenzthiazole was stirred with 8 g (0.25 atom) sulphur and 10.75 g (0.125 mol) dry piperazine in 250 ml isopropanol for 2 hours at room temperature. The mixture was slowly heated to 50°C over a period of 30 minutes and stirred at this temperature for 3 hours. It was then cooled to 0°C, filtered by suction and the residue washed twice with 50 ml isopropanol. Finally the product was dried under vacuum at 50°C. 54 g of a white powder melting at 180°–183°C was obtained. After recrystallisation from dioxane the bis-(2-benzthiazole-dithio)-N,N'-piperazine melted at 187°–188°C.

We claim:
1. Bis-(2-benzthiazole-dithio)-N,N'-piperazine.
2. Bis-(2-benzthiazole-dithio)-N,N'-2,5-dimethyl-piperazine.
3. Bis-(2-benzthiazole-dithio)-N,N'-2,6-dimethyl-piperazine.

* * * * *